(12) United States Patent
Viola et al.

(10) Patent No.: US 11,167,934 B2
(45) Date of Patent: Nov. 9, 2021

(54) CAROUSEL FOR TRANSPORTATION OF ARTICLES

(71) Applicant: M.D. VIOLA MACCHINE S.R.L., Pavia (IT)

(72) Inventors: Davide Viola, Valle Salimbene (IT); Marco Viola, Valle Salimbene (IT); Andrea Viola, Valle Salimbene (IT)

(73) Assignee: M.D. VIOLA MACHINE S.R.L., Valle Salimbene (IT)

( * ) Notice: Subject to any disclaimer, the term of this patent is extended or adjusted under 35 U.S.C. 154(b) by 0 days.

(21) Appl. No.: 17/059,490

(22) PCT Filed: Apr. 11, 2019

(86) PCT No.: PCT/IB2019/052992
§ 371 (c)(1),
(2) Date: Nov. 30, 2020

(87) PCT Pub. No.: WO2019/229551
PCT Pub. Date: Dec. 5, 2019

(65) Prior Publication Data
US 2021/0139252 A1    May 13, 2021

(30) Foreign Application Priority Data
May 31, 2018  (IT) .......................... 102018000005900

(51) Int. Cl.
*B65G 47/244* (2006.01)
*A61F 13/15* (2006.01)
(Continued)

(52) U.S. Cl.
CPC ...... *B65G 47/244* (2013.01); *A61F 13/15764* (2013.01); *B65G 47/848* (2013.01);
(Continued)

(58) Field of Classification Search
CPC .. B65G 47/244; B65G 47/848; B65G 47/915; B65G 2201/022; A61F 13/15764;
(Continued)

(56) References Cited

U.S. PATENT DOCUMENTS 5,660,665 A * 8/1997 Jalonen ............. A61F 13/15601
156/163
8,607,959 B2   12/2013 Papsdorf et al.
(Continued)

FOREIGN PATENT DOCUMENTS

WO     2014/016732 A1    1/2014

OTHER PUBLICATIONS

Aug. 12, 2019 International Search Report issued in International Patent Application No. PCT/IB2019/052992.
(Continued)

*Primary Examiner* — Gene O Crawford
*Assistant Examiner* — Lester Rushin, III
(74) *Attorney, Agent, or Firm* — Oliff PLC (57) ABSTRACT

A carousel for transporting articles includes: a body rotated by a motor around a main axis, a stationary cam around the main axis and a plurality of transfer units mounted on the body to rotate around the main axis. Each unit includes a transfer element having a radially external portion to retain or release an article. The element is pivoted on the body around an auxiliary axis radial to the main axis and is coupled to the body to move along the auxiliary axis. The element is coupled to the stationary cam to rotate around the auxiliary axis. A pair of auxiliary cams is coupled to the element and integral with the body and auxiliary cam-followers are interposed between the element and the auxiliary cam to move on the auxiliary cams during rotation of the element around the auxiliary axis and move the element along the auxiliary axis.

15 Claims, 8 Drawing Sheets

(51) Int. Cl.
  *B65G 47/84*   (2006.01)
  *B65G 47/91*   (2006.01)
  *B65H 29/24*   (2006.01)

(52) U.S. Cl.
  CPC ......... *B65G 47/915* (2013.01); *B65H 29/241* (2013.01); *B65G 2201/022* (2013.01); *B65H 2301/33222* (2013.01); *B65H 2301/4472* (2013.01); *B65H 2301/4473* (2013.01); *B65H 2403/511* (2013.01); *B65H 2801/57* (2013.01)

(58) Field of Classification Search
  CPC .. B65H 2301/33222; B65H 2301/4472; B65H 2301/4473; B65H 2403/511; B65H 2801/57
  USPC ......................................................... 198/411
  See application file for complete search history.

(56) References Cited

U.S. PATENT DOCUMENTS

| | | | |
|---|---|---|---|
| 9,896,294 B2 * | 2/2018 | Ing | B65H 29/243 |
| 9,950,439 B2 * | 4/2018 | McCabe | B26D 7/018 |
| 2013/0152360 A1 | 6/2013 | Schoultz et al. | |

OTHER PUBLICATIONS

Aug. 12, 2019 Written Opinion of the International Searching Authority issued in International Patent Application No. PCT/IB2019/052992.

\* cited by examiner

CAROUSEL FOR TRANSPORTATION OF ARTICLES

FIELD OF THE INVENTION

The present invention relates to a carousel for transportation of articles. Preferably, the transportation carousel according to the present invention finds application in the production/manufacturing lines of articles. Preferably, the transportation carousel according to the present invention is configured for transferring articles coming in succession from a conveyor located upstream of the carousel to a conveyor located downstream, preferably varying, during the path on the carousel, the orientation and/or the pitch of the articles themselves. Preferably but not exclusively, the present invention falls within the scope of production/manufacturing lines of sanitary articles, such as sanitary napkins, diapers, diapers for adults, panty liners, etc.

BACKGROUND ART

Public document U.S. Pat. No. 5,025,910 illustrates an apparatus for rotating sanitary napkins by an angle of 90° around an axis perpendicular to its own plane while these are made to orbit with a drum from a picking station to a transfer station. The apparatus comprises a rotor which carries a plurality of transfer elements supported by spindles and configured to carry the sanitary napkins. The spindles are connected, by pinions and rollers, to a groove of a stationary cam. By rotating the rotor with respect to the stationary cam, the rollers and pinions cause the rotation of each of the transfer elements around a respective axis.

U.S. Pat. No. 6,722,494 discloses a transfer apparatus similar to the previous one wherein the transfer elements are furthermore moved radially and periodically during rotation by a plurality of levers and an additional cam in which respective rollers are engaged.

Document U.S. Pat. No. 7,650,984 illustrates an apparatus for varying the pitch of separation between articles, wherein said apparatus comprises one or more transfer elements for the articles which can perform an orbital movement around a main axis between a picking position and a release position. The speed of the orbital movement is selectively variable in the passage between the picking position and the release position, i.e. each element performs the orbital movement with a law of motion dictated by a respective driving pulley moved by a respective motor. US 2010/0012458 discloses a device similar to the previous one in which the transfer elements are also orientable around a respective axis radially directed with respect to the main axis so as to modify the orientation of the articles in the passage between the picking position and the release position, via a cam formation and a cam-follower element.

U.S. Pat. No. 8,607,959 discloses an apparatus for rotating individual articles during their transfer from a first movable conveyor to a second movable conveyor. The apparatus comprises a plurality of transfer elements movable around a first axis of rotation. Each of the transfer elements is movable towards and away from the first axis of rotation by means of a first guide which surrounds the first axis. Each of the transfer elements is movable in rotation around a second axis perpendicular to the first axis by a second guide which surrounds the first axis and is radially internal to the first guide.

U.S. Pat. No. 9,950,439 discloses an apparatus for receiving, cutting and re-orienting articles, such as sanitary napkins. The apparatus comprises a plurality of transfer elements moved in rotation around a transfer axis. Each transfer element is coupled to a first cam configured to rotate the transfer element and to a second cam configured to vary the pitch. While the transfer element rotates around the transfer axis, the cams alter the position thereof. The first cam alters the motion of the transfer element around an axis of rotation perpendicular to the transfer axis. The second cam alters the circumferential distance between adjacent transfer elements.

OBJECT OF THE INVENTION

The Applicant has observed that the known apparatuses capable of rotating the articles around axes perpendicular to the main axis of rotation and also configured to vary the radial distance of the articles from said main axis of rotation (so as to impart the most suitable law of motion thereto depending on the features of the production line) are structurally very complex and therefore bulky, heavy, expensive to produce and maintain, relatively unreliable.

In particular, the Applicant has observed that the solutions such as those illustrated in U.S. Pat. No. 7,650,984 and US 2010/0012458 comprise as many pulleys as there are transfer elements for moving said transfer elements radially.

The Applicant has also observed that the solutions such as those illustrated in U.S. Pat. Nos. 6,722,494, 8,607,959, 9,950,439 use a cam in which complex linkages are engaged for each of the transfer elements in order to move said transfer elements radially.

In this context, the Applicant has set itself the object of proposing a carousel for transportation of articles that is structurally simpler and, consequently, more compact, lighter, less expensive, easier to assemble and/or maintain, more reliable than those of the prior art.

In particular, the Applicant has set itself the object of proposing a carousel for transportation of articles provided with the advantages mentioned above which is preferably configured to rotate the articles during the transfer around respective axes perpendicular to a main axis of the carousel and also configured to vary a radial distance of said articles from the main axis during the transfer.

SUMMARY OF THE INVENTION

The Applicant has found that these objectives and objects can be achieved by providing a carousel for transportation of articles according to the present invention, of the type claimed in the appended claims and/or described in the following aspects.

In particular, the carousel for transporting articles according to the invention comprises a stationary cam configured to control a rotation movement of the transfer elements around the respective axes perpendicular to the main axis of the carousel during the rotation of the carousel itself and at least one auxiliary cam rotating with the carousel and dedicated to each of the transfer elements to control a radial movement of said transfer elements with respect to the main axis during the rotation of the carousel.

In particular, according to an aspect, the present invention relates to a carousel for transportation of articles, comprising:

a rotating body;
a motor connected to the rotating body to rotate it around a main axis;
at least one stationary cam extending around the main axis;
at least one transfer unit mounted on the rotating body to rotate with said rotating body about the main axis.

Preferably, the carousel comprises a plurality of transport units, for example about ten, mounted on the rotating body to rotate with said rotating body about the main axis.

Preferably, the transfer units are angularly spaced apart from one another.

Preferably, the transfer unit or each transfer unit comprises:
- a transfer element having a radially external portion configured to retain or release an article to be transferred; wherein the transfer element is pivoted on the rotating body about a respective auxiliary axis substantially radial with respect to the main axis; wherein the transfer element is coupled to the rotating body to move along said auxiliary axis; wherein the transfer element is operatively coupled to the stationary cam to rotate about the respective auxiliary axis upon command of the stationary cam.

Preferably, the transfer unit or each transfer unit comprises:
- at least one auxiliary cam operatively coupled to the transfer element and integral with the rotating body;
- an auxiliary cam-follower operatively interposed between the transfer element and the auxiliary cam, wherein the auxiliary cam-follower is configured to run on the auxiliary cam during the rotation of the transfer element around the respective auxiliary axis; wherein the auxiliary cam is configured to move the transfer element along the respective auxiliary axis.

The rotation movement of each transfer element around the respective axis perpendicular to the main axis of the carousel is produced by the relative motion of the transfer element with respect to the stationary cam during the rotation of the carousel.

The radial movement of the transfer element with respect to the main axis is produced by the relative motion of the transfer element with respect to the auxiliary cam in turn generated by the movement of rotation of the transfer element around the respective auxiliary axis perpendicular to the main axis.

It follows that a single motor which rotates the carousel is able to produce both the rotational movement of each transfer element around the respective auxiliary axis and the radial movement of the transfer element with respect to the main axis.

The Applicant has verified that the solution according to the invention allows first of all the movement of the transfer element(s) along an orbital trajectory and with a determined law of motion through a relatively simple structure of the carousel. The Applicant has therefore verified that the carousel according to the invention is:
- structurally less complex than those of the prior art;
- lighter and more compact than those of the prior art;
- more reliable and easier to maintain than those of the prior art;
- more cost-effective to make, since the elements that make it up are fewer and less expensive, so that the time required for the assembly thereof is also reduced.

The Applicant has also verified that the carousel according to the invention ensures accuracy and fluidity of the movements of its parts and allows transmitting the forces and torques from the motor to the transfer elements in an effective and efficient manner.

The Applicant has also verified that, by appropriately shaping the stationary cam and/or the auxiliary cam(s), it is possible to define the law of motion of the transfer element(s) and of the articles transferred according to the specific application, to transfer and vary the orientation and/or pitch of said articles.

Further aspects of the invention are described below.

In one aspect, the motor connected to the rotating body to put it in rotation is only one.

In one aspect, the rotating body is a disc, preferably annular.

In one aspect, the stationary cam comprises a cylinder coaxial to the rotating body and having at least one track formed on a radially external surface of the cylinder.

In one aspect, the rotating body is arranged around the cylinder.

In one aspect, the transfer unit or each transfer unit comprises a guide spindle extending along the auxiliary axis and rotatable around said auxiliary axis.

In one aspect, the transfer element is slidably mounted on the guide spindle to translate along the auxiliary axis and rotate together with the guide spindle around the auxiliary axis.

In one aspect, a main cam-follower integral with the guide spindle is engaged with the stationary cam.

In one aspect, the main-cam follower comprises an arm connected to the guide spindle and a wheel engaged with the main cam, preferably housed in said at least one track.

In one aspect, the main cam-follower is mounted on a radially internal end of the guide spindle.

In one aspect, the transfer unit or each transfer unit comprises at least one bracket integral with the main body and rotatably supporting the guide spindle.

In one aspect, the transfer unit or each transfer unit comprises a hollow body integral with the rotating body and at least partially housing the transfer element.

In one aspect, the auxiliary cam is formed in a wall of the hollow body.

In one aspect, the transfer element comprises a cylindrical body partially inserted in the hollow body and inserted on the guide spindle.

In one aspect, the cylindrical body carries the radially external portion at one end thereof.

In one aspect, the auxiliary cam-follower is integral with said cylindrical body.

In one aspect, the auxiliary cam develops at least partially around the respective auxiliary axis.

In one aspect, the auxiliary cam is defined by a groove formed in a wall of the hollow body.

In one aspect, the auxiliary cam-follower comprises at least one pin integral with the respective transfer element and engaged with the auxiliary cam.

In one aspect, said at least one pin extends radially from the cylindrical body of the transfer element.

In one aspect, the auxiliary cam has a substantially helical development.

In one aspect, the auxiliary cam develops obliquely on the wall of the hollow body by a predefined angle. The rotation of the transfer element around the auxiliary axis is equal to said predefined angle. Preferably but not exclusively, said predefined angle is about 90°.

In one aspect, the transfer unit or each transfer unit comprises a plurality of auxiliary cams, each engaged by a respective pin.

In one aspect, the transfer unit or each transfer unit comprises two auxiliary cams, preferably located on radially opposite sides of the auxiliary axis and each engaged by a respective pin.

In one aspect, the cylindrical body of the transfer element comprises two diametrically opposed pins, each engaged in one of the two auxiliary cams.

The Applicant has verified that the distribution of several auxiliary cams and respective pins around the auxiliary axis enables the torque applied to the articles to be distributed more efficiently through the transfer elements.

In one aspect, the carousel comprises a pneumatic device in fluid communication with at least one internal chamber of the radially external portion.

In one aspect, the pneumatic device is in fluid communication with said at least one internal chamber through the hollow body and the cylindrical body.

In one aspect, the rotating body has a through opening in fluid communication with the hollow body of the or of each transfer unit.

In one aspect, the pneumatic device is connected to the through holes or openings on a rear side of the rotating body opposite to a front side carrying the transfer unit(s).

In one aspect, the rear side of the rotating body delimits with a fixed portion one or more distribution chambers in fluid communication with the through openings and connected to the pneumatic device.

In one aspect, the distribution chambers are divided into overpressure chambers and depression chambers.

During the rotation of the carousel, the or each transfer unit and in particular the hollow body subsequently enters in fluid communication with the distribution chambers, which are fixed, and therefore the holes of the perforated surface suction or blow air according to the angular position of the respective transfer element.

The structure of the carousel therefore integrates the conduits for the fluid (preferably air) and this helps to contain the size of the assembly and to reduce the weight thereof.

In one aspect, the radially external portion has a perforated surface in fluid communication with said at least one internal chamber.

In one aspect, the perforated surface is configured to hold the article by depression.

In one aspect, the pneumatic device is configured to generate a depression to retain the article on the perforated surface.

In one aspect, the pneumatic device is configured to generate an overpressure to move the article away from the perforated surface.

In one aspect, the perforated surface has distinct groups of holes.

In one aspect, said at least one internal chamber comprises a plurality of internal chambers defining a fluid path, to generate a differentiated pressure or depression at the different groups of holes.

In one aspect, a first group of holes is positioned at an end edge of the perforated surface and at a first chamber directly connected to the cylindrical body.

In one aspect, the different groups of holes and/or internal chambers described and/or claimed hereinabove may also be present in a carousel provided with transfer units of a structure different from that described and claimed herein. The different groups of holes and/or internal chambers may therefore define an independent invention.

According to a further aspect thereof, the present invention relates to an apparatus for manufacturing articles, comprising:

a first conveyor, preferably a first conveyor belt;
    a second conveyor, preferably a second conveyor belt;
    a carousel for transportation of articles made according to one or more of the preceding aspects and/or the appended claims;
    wherein the carousel is located between the first conveyor and the second conveyor for picking the articles from one end of the first conveyor and taking them to one end of the second conveyor, preferably varying the orientation and/or the pitch thereof.

In one aspect, the end of the first conveyor and the end of the second conveyor are located in diametrically opposed positions of the carousel.

In one aspect, a rotation angle of the carousel around the main axis to carry the articles from the end of the first conveyor to the end of the second conveyor is about 180° but it may also be a different angle.

In one aspect, the apparatus is configured to manufacture articles of flattened shape and preferably soft and/or flexible.

In one aspect, the apparatus is configured to manufacture sanitary articles, more preferably diapers, sanitary napkins, panty liners.

In one aspect, during the rotation of the carousel, the end of the first conveyor is first engaged by the first group of holes which are obstructed by the incoming article.

In this way, a greater depression is first exerted at the first group of holes where it serves to retain the incoming article. Once a portion of the article has obstructed the first group of holes, the depression is also distributed to the other group(s) receiving the remaining portion of the said article. This allows the articles to be picked up and removed in a more precise and effective manner, avoiding, for example, the formation of creases on the articles.

In one aspect, the end of the second conveyor has a substantially flat receiving surface of the article released from the carousel.

In one aspect, said receiving surface is parallel to the perforated surface of the transfer element which is in front of it. In this way, the article released from the carousel adheres immediately to the second conveyor completely.

In one aspect, the receiving surface described and/or claimed herein may also be present in a carousel provided with transfer units and/or transfer elements of a structure different from those described and claimed herein. The second conveyor with said receiving surface may therefore define an independent invention.

Further features and advantages will appear more clearly from the detailed description of a preferred but non-exclusive embodiment of a carousel for transportation of articles according to the present invention.

BRIEF DESCRIPTION OF THE DRAWINGS

Such description is given hereinafter with reference to the accompanying drawings, provided only for illustrative and, therefore, non-limiting purposes, in which.

DETAILED DESCRIPTION OF PREFERRED EMBODIMENTS OF THE INVENTION

With reference to the accompanying figures, reference numeral indicates as a whole a carousel for transportation of articles 2 according to the present invention combined with a first conveyor belt 3 placed upstream of the carousel 1 and a second conveyor belt 4 placed downstream of the carousel 1, with respect to a feeding direction of the articles 2.

The carousel 1, the first conveyor belt 3 and the second conveyor belt 4 are part of an apparatus for manufacturing articles for example configured for the production of sanitary articles, such as diapers, sanitary napkins, diapers for adults, panty liners, etc. The articles 2, schematically illustrated in the accompanying figures, are soft and flexible semi-finished products with a rectangular flattened shape. The remaining parts of the apparatus have not been illustrated since they can be of a known type.

The carousel 1 is located between the first conveyor belt 3 and the second conveyor belt 4 for picking the articles 2 successively from one end 5 of the first conveyor belt 3 and carrying them to an end 6 of the second conveyor belt 4.

The articles 2 are preferably retained on the respective conveyor belts 3, 4 by means of a depression generated through holes in the belts, not illustrated since they are of a type known per se.

During the transport operated by the carousel 1, the articles 2 are rotated and brought closer to a main axis "X-X" of the carousel 1 itself to vary the orientation and the pitch according to the subsequent manufacturing operations.

Figure 1:
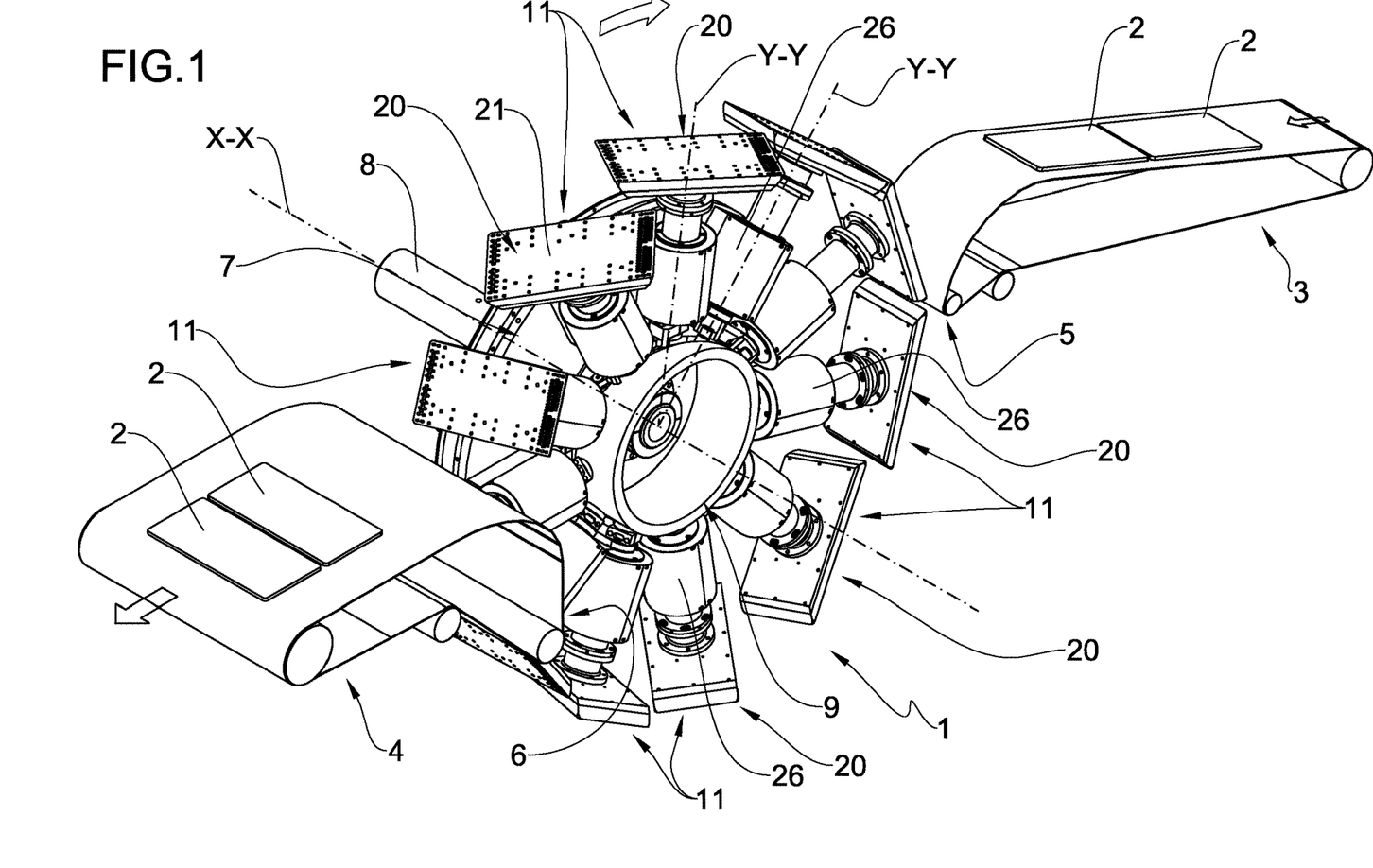
FIG. 1 shows a front perspective view of a carousel for transportation of articles according to the present invention associated with two conveyors.
Figure 2:
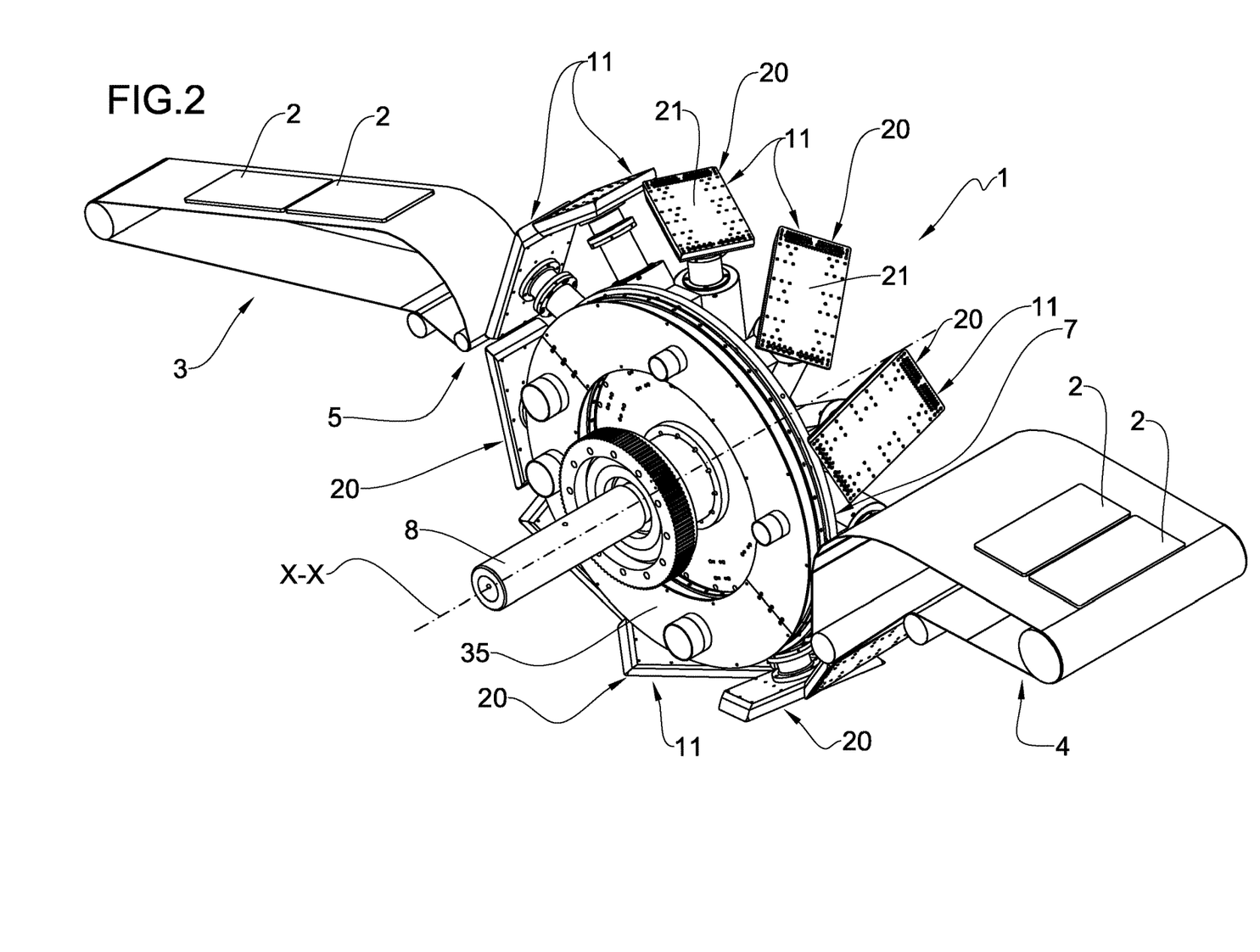
FIG. 2 shows a rear perspective view of the carousel in FIG. 1.
Figure 3:
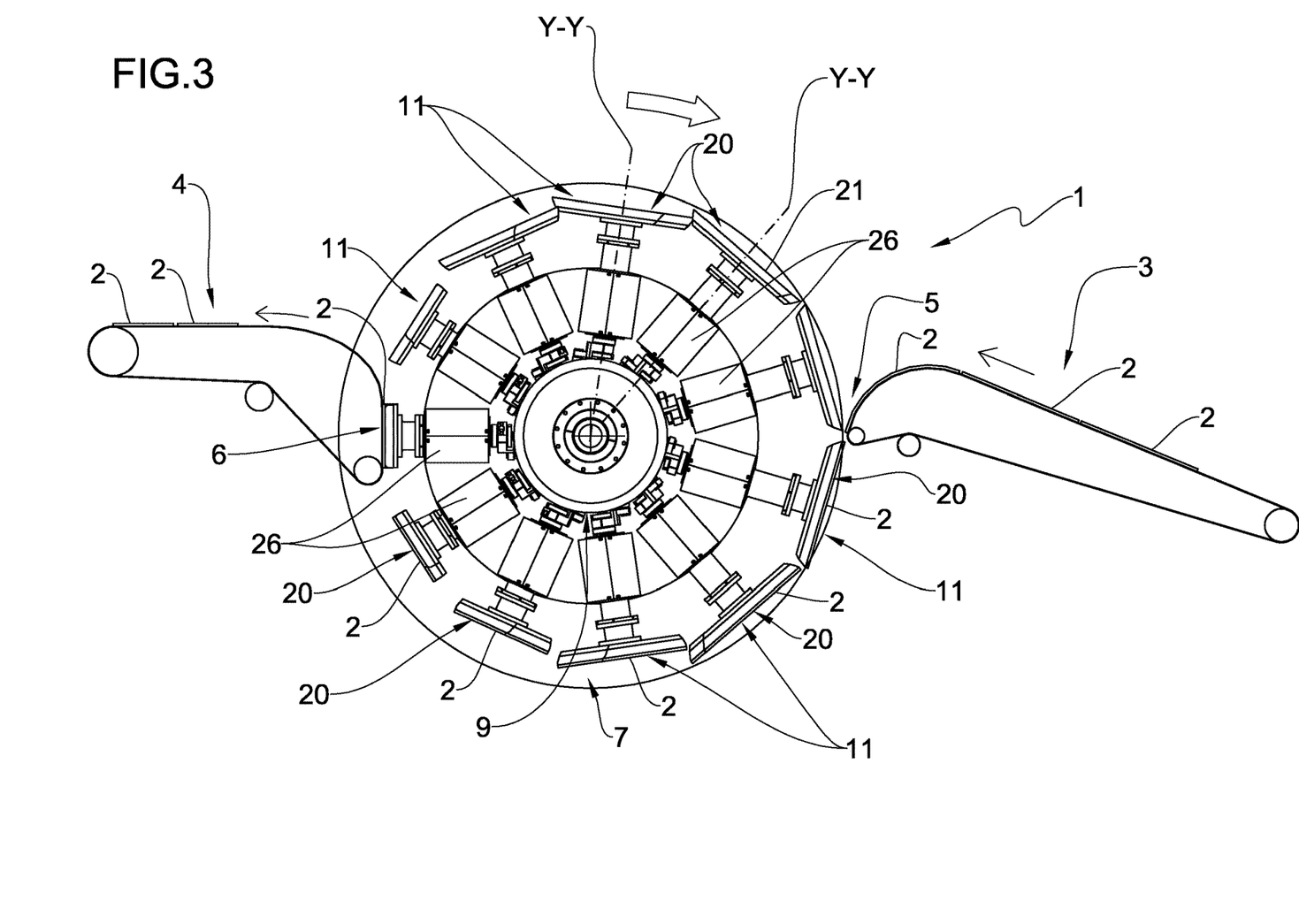
FIG. 3 shows a front view of the carousel in FIGS. 1 and 2.

As shown in the accompanying FIGS. 1, 2 and 3, the articles 2 on the first conveyor belt 3 are oriented with their largest dimension aligned with the feeding direction whereas on the second conveyor belt 4, the major dimension of the articles 2 is transverse with respect to the feeding direction. In the non-limiting example illustrated, during the transfer on the carousel 1, the articles 2 are rotated by 90° and moved closer to each other, for example to keep the mutual distance constant, or to increase or decrease it.

The carousel 1 comprises a rotating body 7 shaped like an annular disc coaxial to the aforementioned main axis "X-X" and mounted on a spindle 8 connected to an electric motor, not shown. The motor is configured to rotate the rotating body 7 around the main axis "X-X".

The carousel 1 comprises a fixed cylinder 9 (not rotating with the rotating body 7) coaxial with the rotating body 7 and located in a radially internal position with respect to the rotating body 7. The cylinder 9 has a track 10 defined by a groove formed on a radially external surface thereof. The track 10 extends all around the main axis "X-X" and is shaped according to the rotation movement that must be imparted to the articles 2. The cylinder 9 with the track 10 defines a stationary cam extending around the main axis "X-X".

The carousel 1 comprises a plurality of transfer units 11 mounted on a front face of the rotating body 7 and around the cylinder 9 to rotate with said rotating body around the main axis "X-X". In the non-limiting embodiment shown, the transfer units 11 are eleven, angularly spaced from each other and each one extending mainly along a radial direction.

The transfer units 11 are identical to each other so only one will be described in detail hereinafter.

Figure 4:
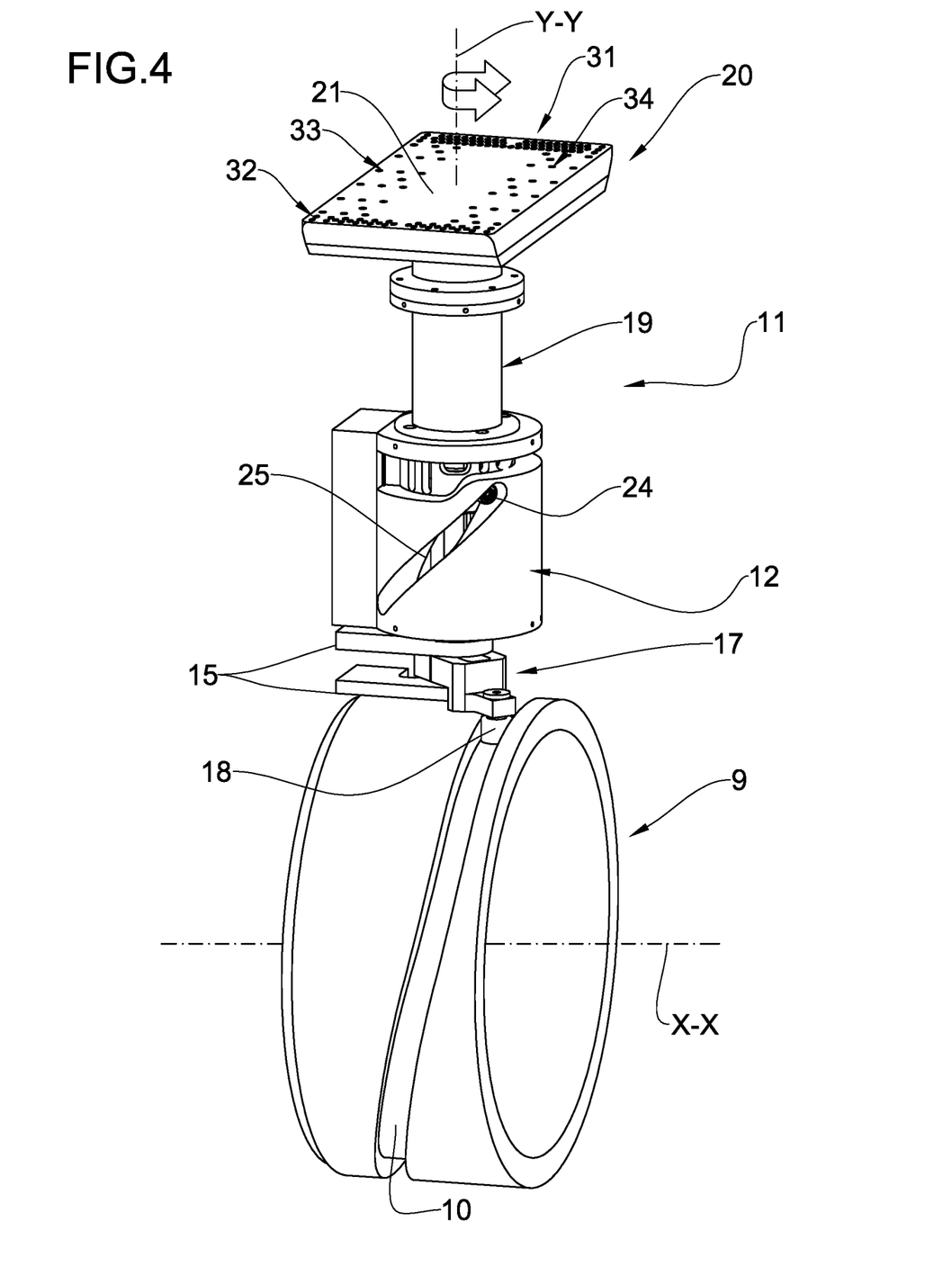
FIG. 4 is a perspective view of a group of elements of the carousel in the previous figures.

The transfer unit 11 comprises a hollow body 12 integral with the rotating body 7. According to what is best illustrated in FIG. 4, the hollow body 12 has a substantially cylindrical shape and is joined laterally to the front face of the rotating body 7. At the junction area, the hollow body 12 has a passage 13 communicating with a respective through opening 14 formed in the rotating body 7.

In a radially internal position with respect to the hollow body 12 there is a pair of brackets 15 parallel to each other, joined to the front face of the rotating body 7 and extending away and projecting from said rotating body 7. The brackets 15 rotatably support a guide spindle 16 which extends along a respective auxiliary radial axis "Y-Y", that is, perpendicular to the main axis "X-X". The guide spindle 16 can rotate around the respective auxiliary axis "Y-Y" and extends inside the hollow body 12, coaxially therewith.

On a radially internal end of the guide spindle 16 there is mounted a main cam-follower 17 engaged in the track 10 of the stationary cam 9. The main cam-follower 17 comprises an arm connected to the guide spindle 16. The arm carries a wheel 18 engaged in the track 10. An axis of rotation of the wheel 18 is offset from the auxiliary axis "Y-Y" and the arm rotates integrally with the guide spindle 16.

A transfer element comprising a cylindrical body 19 which is partially housed in the hollow body 12 is inserted on the guide spindle 16 so as to slide. The cylindrical body 19 carries on a radially external end a radially external portion 20 configured to retain or release an article 2 to be transferred. The radially external portion 20 is shaped like a sort of plate and has a perforated surface 21 orthogonal to the auxiliary axis "Y-Y".

The perforated surface 21 has in plan a shape similar to that of the articles 2 to be transferred. The radially external portion 20 defines internal chambers in fluid communication with holes in the perforated surface and with a volume inside the cylindrical body 19.

A seal 22 is positioned at a radially internal end of the cylindrical body 19 through which the guide spindle 16 passes in order to slide. The coupling between the seal 22, which is integral with the cylindrical body 19, and the guide spindle 16 is such that said cylindrical body 19 and the respective radially external portion 20 can translate along the auxiliary axis "Y-Y" with respect to the guide spindle 16 and rotate together with the guide spindle 16 around the auxiliary axis "Y-Y".

The seal 22 defines the aforementioned volume inside the cylindrical body 19. Radial holes 23 pass through the cylindrical body 19 and put the internal volume in communication with the inside of the hollow body 12 and then with the passage 13.

At the seal 22, two diametrically opposed pins 24 are installed which project radially towards the outside of the cylindrical body 19. Each of the two pins 24 is engaged in respective grooves 25 formed in a wall of the hollow body 12. Each of the two grooves 25, one of which is visible in FIG. 4, develops partially around the auxiliary axis "Y-Y" by an angle of about 90° along a helical path stretch, from a lower portion of the hollow body 12 towards an upper portion of the hollow body 12. The two grooves 25 define respective auxiliary cams and the two pins 24 define respective auxiliary cam-followers.

An external jacket 26, visible only in FIGS. 1 and 3, surrounds the wall of the hollow body 12 to seal the inside of the hollow body 12.

Figure 6:
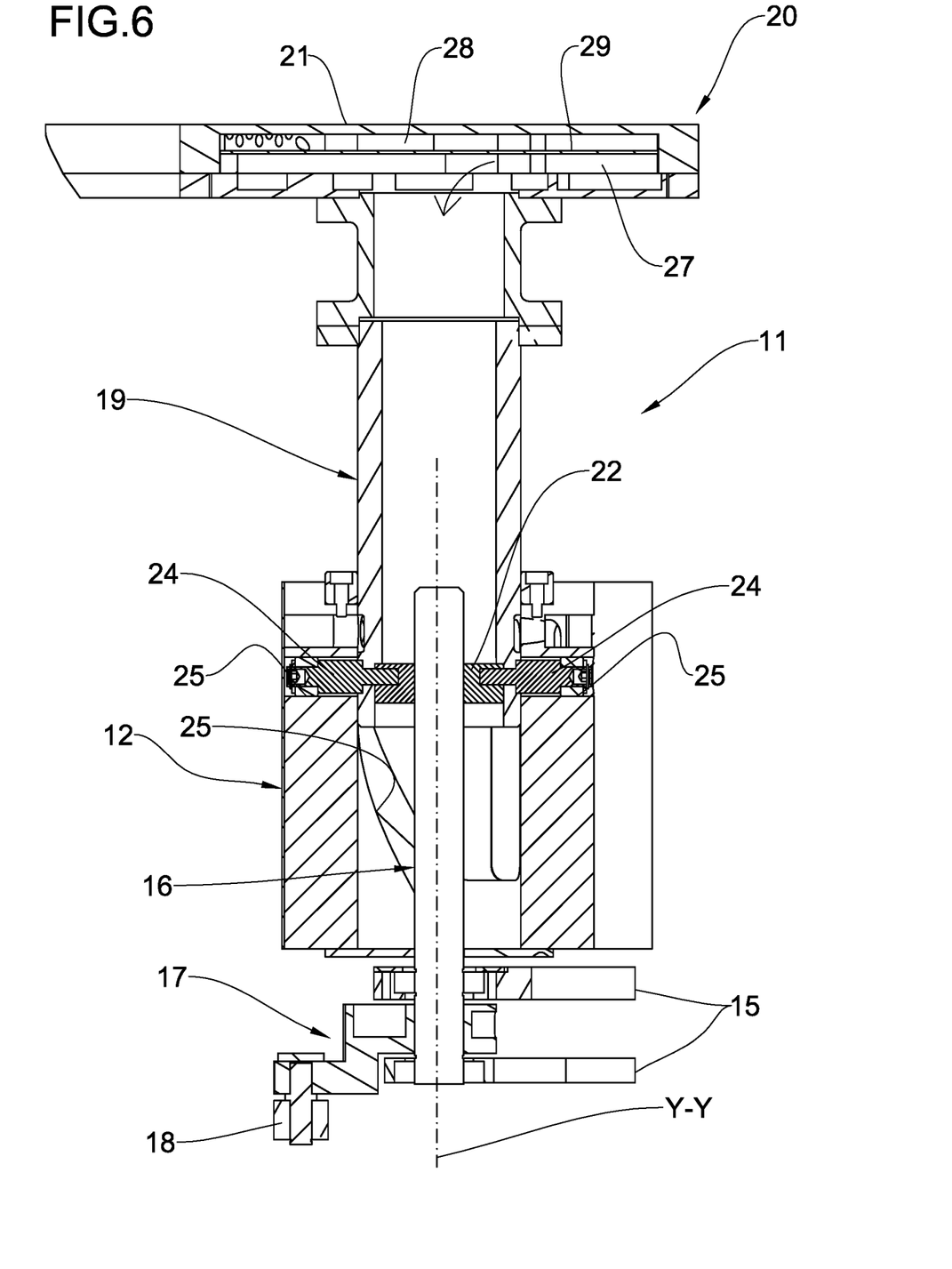
FIG. 6 is a sectional view of a part of the group in FIG. 5.
Figure 7:
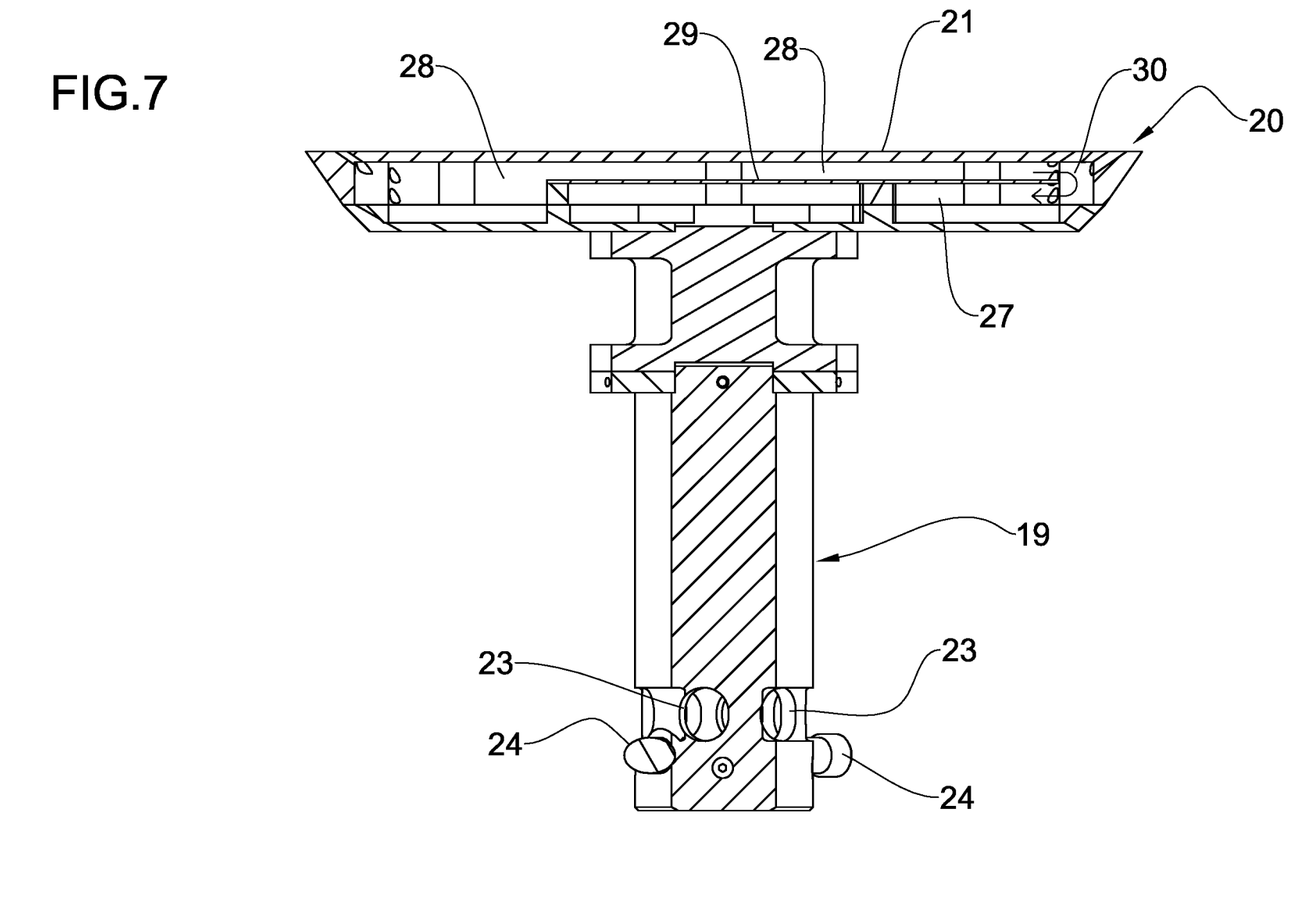
FIG. 7 is a sectional view of one of the elements of the group in FIGS. 4, 5 and 6.
Figure 8:
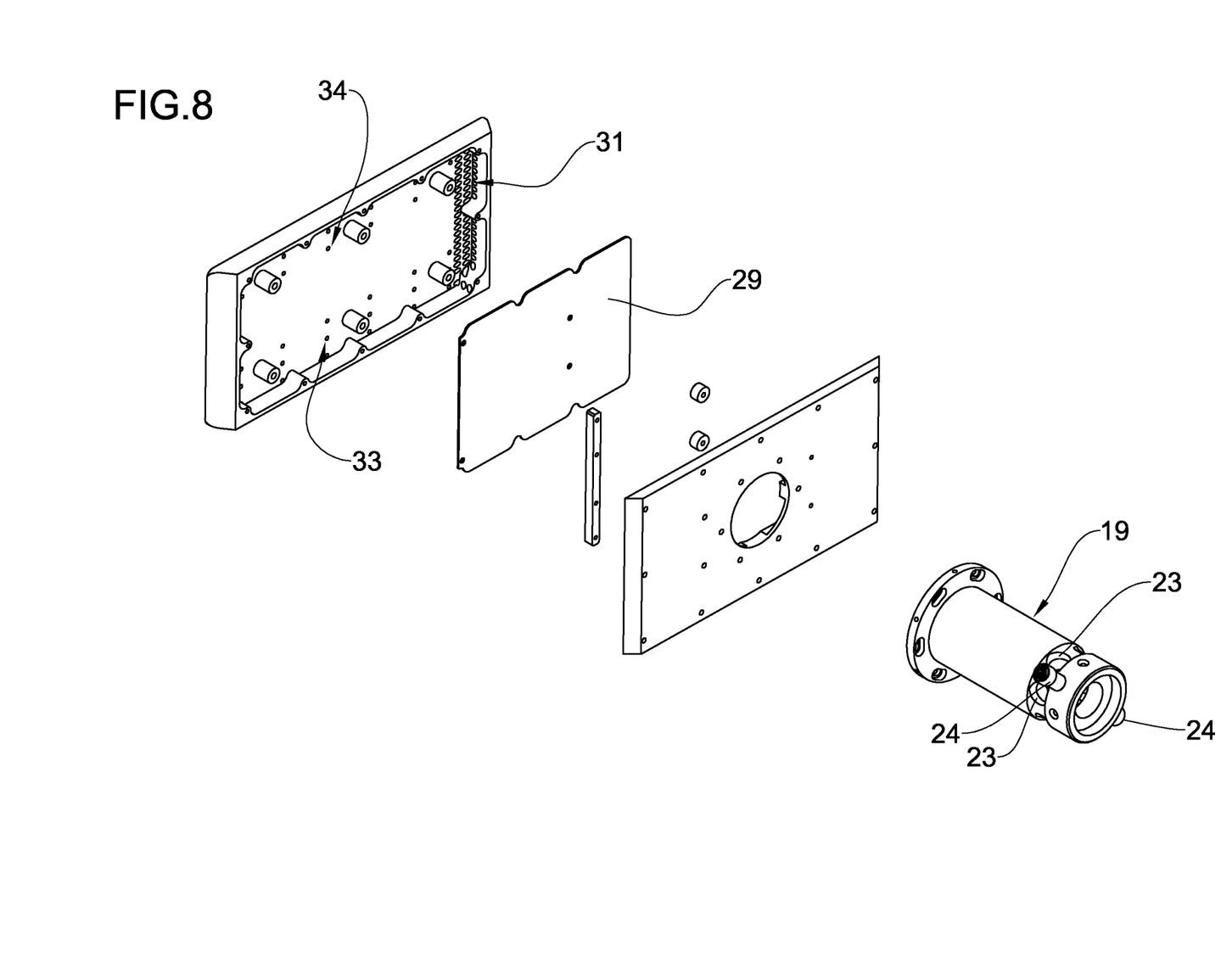
FIG. 8 shows an exploded view of the element in FIG. 7.

As better illustrated in FIGS. 6 and 7, the radially external portion 20 delimits at its interior a first chamber 27 and a second chamber 28 separated by a partition 29.

The partition 29 is parallel to the perforated surface 21. Holes in the perforated surface open directly into the second chamber 28. The volume inside the cylindrical body 19 opens directly into the first chamber 27. The first chamber 27 communicates with the second chamber 28 through a slot 30 formed inside the radially external portion 20 and at an end edge of the perforated surface 21 (FIG. 7). The first and second chambers 27, 28 define a path for the fluid which, suctioned through the holes, passes through the second chamber 28, then through the slot 30, the first chamber 27, even into the cylindrical body 19 or which blown through the cylindrical body 19, passes through the first chamber 27, then through the slot 30, in the second chamber 28 and through the holes.

The perforated surface 21 has distinct groups of holes (FIG. 4). A first group of holes 31 is located at the aforementioned end edge of the perforated surface 21 and therefore near the internal slot 30. A second group of holes 32 is located at an opposite end edge of the perforated surface 21. A third and a fourth group of holes 33, 34 are located at the side edges of the perforated surface. This structure allows generating a differentiated pressure or depression at the different groups of holes 31, 32, 33, 34.

Figure 5:
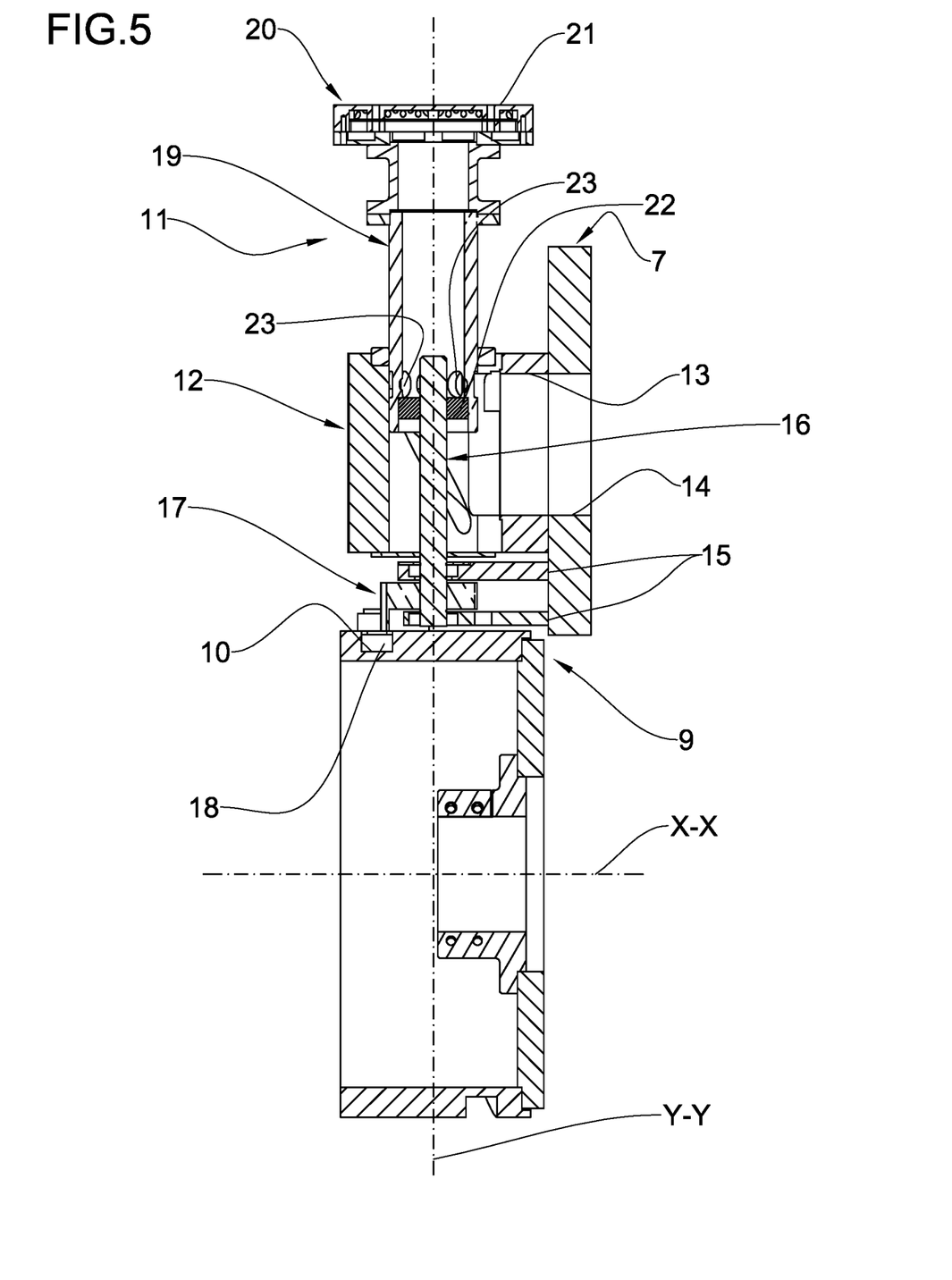
FIG. 5 is a sectional view of the group in FIG. 4.

For this purpose, the carousel 1 comprises a pneumatic device, not shown, in fluid communication with the first and second chamber 27, 28 of the radially external portion through the through opening 14, the passage 13, the hollow body 12, the radial holes 23 and the cylindrical body 19 (FIG. 5). The rear side of the rotating body 7 delimits with a fixed portion 35 (FIG. 2) one or more distribution chambers, internal and not visible in the accompanying figures, in fluid communication with the through openings 14 and connected to the pneumatic device. The aforementioned distribution chambers are divided into overpressure chambers and depression chambers, so that, during the rotation of the carousel 1, each transfer unit 11 subsequently enters in fluid communication with the distribution chambers, which are fixed, and therefore the holes of the perforated surface suction or blow air according to the angular position of the respective transfer element.

In operation, the motor keeps the rotating body 7 rotating around the main axis "X-X" at a constant speed and in a clockwise direction (referring to FIG. 3).

The transfer units 11 rotate together with the rotating body 7 and the wheel 18 of each transfer unit 11 follows the track 10 of the stationary cam 9 by turning the respective transfer element around the respective auxiliary axis "Y-Y" according to the angular position of the transfer unit 11 around the main axis "X-X".

The rotation of the transfer element around the respective auxiliary axis "Y-Y" in turn causes a displacement of the two pins 24 in the respective grooves 25 and therefore a translation of the transfer element along the respective auxiliary axis "Y-Y", i.e. along a radial direction with respect to the main axis "X-X".

In the exemplary and non-limiting example illustrated, the shapes of the track 10 and the grooves 25 are such that each radially external portion 20 lies in a radially outermost position and with the major dimension thereof oriented in a circumferential direction when it is near the first conveyor 3 and lies in a radially more internal position and with the minor dimension thereof oriented in a circumferential direction when it is near the second conveyor 4. During the clockwise rotation by about 180° between the first conveyor 3 and the second conveyor 4, each radially external portion 20 rotates around the respective auxiliary axis "Y-Y" by 90° and moves radially along the respective auxiliary axis "Y-Y" towards the main axis "X-X". In the subsequent path by a further 180° towards the first conveyor 3, each radially external portion 20 rotates around the respective auxiliary axis "Y-Y" in an opposite direction and by 90° and moves radially along the respective auxiliary axis "Y-Y" away from the main axis "X-X".

The first conveyor belt 3 supports on an upper branch thereof and feeds in sequence a plurality of articles 2 towards the end 5 thereof.

Each radially external portion 20 approaches first the end of the first conveyor 3 with its end edge of the perforated surface 21 provided with the first group of holes 31 while the first and second chambers 27, 28 are in depression and the major depression is concentrated at the slot 30 or at the first group of holes 31. The first group of holes 31 engages the article 2 placed on the end 5 of the first conveyor belt 3 and retains it on the perforated surface 21. Since the first group of holes 31 is closed by the article 2 being picked, the depression is redistributed on the remaining groups of holes on which the whole article 2 is gradually placed.

The article 2 substantially covers all the perforated surface 21 and is retained thereon by depression.

Such a depression is maintained, thanks to the distribution chambers, until the radially external portion 20 with the article 2 reaches the end of the second conveyor belt 4.

As can best be seen in FIG. 3, the second conveyor belt 4 is shaped (by means of rollers and guides) so as to have a flat portion tangent to a circumference with a center in the main rotation axis "X-X". Said flat section has a substantially flat receiving surface 36 of the article 2 released from the carousel 1. Said receiving surface 36 is parallel to the perforated surface 21 of the radially external portion 20 which is in front of it.

When the radially external portion 20 with the article 2 faces the receiving surface 36, the pneumatic device, thanks to the distribution chambers, generates an overpressure which blows the article 2 against the receiving surface 36 which in turn it retains it thanks to its own depression. In this way, the article 2 released from the carousel 1 immediately adheres completely to the second conveyor 4 which then transfers it on an upper branch thereof away from the carousel 1.

The invention claimed is:
1. Carousel for transportation of articles, including:
   a rotating body;
   a motor connected to the rotating body to rotate it around a main axis;
   at least one stationary cam extending around the main axis
   at least one transfer unit mounted on the rotating body to rotate with the rotating body about the main axis;
   wherein the transfer unit or each transfer unit comprises:
   a transfer element having a radially external portion configured to retain or release an article to be transferred; wherein the transfer element is pivoted on the rotating body about a respective auxiliary axis substantially radial with respect to the main axis; wherein the transfer element is coupled to the rotating body to move along the auxiliary axis; wherein the transfer element is operatively coupled to the stationary cam to rotate about the respective auxiliary axis upon command of the stationary cam;
   wherein it comprises
   at least one auxiliary cam operatively coupled to the transfer element and integral with the rotating body; wherein the auxiliary cam develops at least partially around the respective auxiliary axis;

an auxiliary cam-follower operatively interposed between the transfer element and the auxiliary cam, wherein the auxiliary cam-follower is configured to run on the auxiliary cam during the rotation of the transfer element around the respective auxiliary axis; wherein the auxiliary cam is configured to move the transfer element along the respective auxiliary axis.

2. Carousel according to claim 1, wherein the auxiliary cam has a substantially helical development.

3. A carousel according to claim 1, wherein the auxiliary cam-follower comprises at least one pin integral with the respective transfer element and engaged with the auxiliary cam.

4. A carousel according to claim 1, wherein the transfer unit or each transfer unit comprises two auxiliary cams and the auxiliary cam-follower comprises two pins, each engaged with one of the two auxiliary cams.

5. A carousel according to claim 4, wherein the two pins are diametrically opposed.

6. A carousel according to claim 1, wherein the transfer unit or each transfer unit comprises a hollow body integral with the rotating body and at least partially housing the transfer element.

7. A carousel according to claim 6, wherein the auxiliary cam is formed in a wall of the hollow body.

8. A carousel according to claim 1, wherein the transfer unit or each transfer unit comprises:
a guide spindle extending along the auxiliary axis and rotating about the auxiliary axis; wherein the transfer element is slidably mounted on the guide spindle to translate along the auxiliary axis and rotate together with the guide spindle about the auxiliary axis.

9. A carousel according to claim 8, comprising a main cam-follower integral with the guide spindle and engaged with the stationary cam.

10. A carousel according to claim 9, wherein the main cam-follower comprises an arm connected to the guide spindle and a wheel engaged with the main cam.

11. A carousel according to claim 8, wherein the transfer unit or each transfer unit comprises a hollow body integral with the rotating body and at least partially housing the transfer element, wherein the transport element comprises a cylindrical body partially inserted into the hollow body and inserted on the guide spindle; wherein the cylindrical body carries the radially external portion at one end thereof.

12. A carousel according to claim 11, wherein the auxiliary cam-follower integral with said cylindrical body.

13. A carousel according to claim 12, comprising a pneumatic device in fluid communication with the hollow body, with the cylindrical body and with at least one internal chamber of the radially external portion; wherein the radially external portion has a perforated surface in fluid communication with the at least one internal chamber and configured to retain the article by depression.

14. A carousel according to claim 13, wherein the perforated surface has groups of holes; wherein the at least one internal chamber comprises a plurality of internal chambers defining a fluid path for generating a differentiated pressure or depression at different groups of holes.

15. Apparatus for manufacturing articles, comprising:
a first conveyor;
a second conveyor;
a carousel for transportation of articles made according to claim 1;
wherein the carousel is located between the first conveyor and the second conveyor for picking the articles from one end of the first conveyor and taking them to one end of the second conveyor varying the orientation and/or the pitch thereof.

* * * * *

UNITED STATES PATENT AND TRADEMARK OFFICE
CERTIFICATE OF CORRECTION

| | |
|---|---|
| PATENT NO. | : 11,167,934 B2 |
| APPLICATION NO. | : 17/059490 |
| DATED | : November 9, 2021 |
| INVENTOR(S) | : Davide Viola et al. |

It is certified that error appears in the above-identified patent and that said Letters Patent is hereby corrected as shown below:

On the Title Page

Item (71) should read:
M.D. VIOLA MACCHINE S.R.L., Valle Salimbene (IT)

Item (73) should read:
M.D. VIOLA MACCHINE S.R.L., Valle Salimbene (IT)

Signed and Sealed this
Thirty-first Day of May, 2022

Katherine Kelly Vidal
*Director of the United States Patent and Trademark Office*